United States Patent [19]

Bass et al.

[11] Patent Number: 5,292,362

[45] Date of Patent: * Mar. 8, 1994

[54] TISSUE BONDING AND SEALING COMPOSITION AND METHOD OF USING THE SAME

[75] Inventors: Lawrence S. Bass, Little Neck, N.Y.; Steven K. Libutti, Fort Lee, N.J.; Alexander M. Eaton, Durham, N.C.

[73] Assignee: The Trustees of Columbia University in the City of New York, New York, N.Y.

[*] Notice: The portion of the term of this patent subsequent to May 11, 2010 has been disclaimed.

[21] Appl. No.: 727,607

[22] Filed: Jul. 9, 1991

Related U.S. Application Data

[63] Continuation-in-part of Ser. No. 560,069, Jul. 27, 1990, Pat. No. 5,209,776.

[51] Int. Cl.$^5$ .................... C09J 189/00; C09J 199/00
[52] U.S. Cl. .................... 106/124; 106/126; 106/128; 106/135; 106/137; 106/157; 106/158; 106/161; 106/162; 106/178; 106/217; 106/287.2; 106/287.21; 106/287.35; 514/773; 514/776; 606/214
[58] Field of Search ............... 106/124, 126, 128, 135, 106/137, 157, 158, 161, 162, 178, 217, 287.2, 287.21, 287.35; 514/773, 776; 606/214

[56] References Cited

U.S. PATENT DOCUMENTS

| | | |
|---|---|---|
| 3,438,374 | 4/1969 | Falb et al. |
| 4,122,853 | 10/1978 | Smith |
| 4,362,567 | 12/1982 | Shwarz et al. |
| 4,414,976 | 11/1983 | Schwarz et al. |
| 4,550,238 | 10/1985 | Van Herle et al. |
| 4,625,724 | 12/1986 | Suzuki |
| 4,633,870 | 1/1987 | Saver |
| 4,657,820 | 4/1987 | Halpern et al. ............... 106/157 |
| 4,672,969 | 6/1987 | Dew |
| 4,676,790 | 6/1987 | Kern |
| 4,782,819 | 11/1988 | Adair |
| 4,818,291 | 4/1989 | Iwatsuki et al. |
| 4,854,320 | 8/1989 | Dew et al. |
| 4,909,251 | 3/1990 | Seelich |

OTHER PUBLICATIONS

CA85(19):138042h, Gorog et al, 1976 (no month avail.).
K. K. Jain "Repair of small blood vessels with the neodyomium yag laser" Surgery vol. 85 No. 6 pp. 684–688 (1979) (no month avail.).
R. L. Burleson et al "Fibrin Adherence to biologic tissues" J. Surg. Research 25,523–529 (1978) (no month avail.).
Khalid J. Awan et al "use of Isobutyl -2- Cyanoacrylate tissue adhesive" Annals of Opth pp. 851–853 (Aug. 1974).
J. A. Fayez et al "Tubal Microsurgery with the Carbon dioxide Laser" Am. J. obster. Gynecol 146/4 (1983) (no month avail.).
G. F. Gestring et al "Autologoos Fibrinogen for tissue adhesion . . . " Vas. Surg pp. 294–304 (Sep./Oct. 1983).
F. X. Brunner "Histological findings in sutured and fibrin-glued Microvascular Anastomosis" A. Otor. 240;311–318 (1984) (no month avail.).
J. A. Fayez et al "Comparison of Tubal Surgery with the co2 Laser . . . " Fert. and Ster. vol. 40 No. 4 (Oct. 1983).
J. K. Choe et al "Clinical and Histological evaluation of Laser Reanastomosis . . . " Fert. and Ster. vol. 41 No. 5 (May 1984).
E. L. Smith et al "Principles of Biochemistry" 7th Edition pp. 7 and 229 (1983) (no month avail.).
R. R. Krueger et al "Argon Laser Coagulation of Blood for the Anastomosis of small vessels" Laser in Surg. ±Med 5:55–60 1985 (no month available).
(List continued on next page.)

*Primary Examiner*—David Brunsman
*Attorney, Agent, or Firm*—John P. White

[57] ABSTRACT

Disclosed is a composition for bonding separated tissues together or for coating tissues or prosthetic materials including at least one natural or synthetic peptide and at least one support material which may be activated by energy and to methods of making and using the same.

42 Claims, No Drawings

OTHER PUBLICATIONS

K. H. Siedentor et al "Autologous Fibrin Tissue Adhesive" Laryngoscope 95:1074–1076 (Sep. 1985).

J. S. Saver et al "Bursting Pressures of CO2 Laser—Welded Rabbit Ileum" Lasers in Surg ± Med 6:106–109 (1986) (no month avail.).

J. W. Baker et al "A technique for spray application of Fibrin Glue . . . " Ann. Thorac. Surg 43:564–65 (May 1987).

D. J. Coleman Et al "A Biologic Tissue Adhesive for vitreoretinal surgery" Retina vol. 8 No. 4:250–256 (1986–88) (no month avail.).

A. Hjortrup et al "Fibrin Adhesive versus sutured Anastomosis . . . " Br. J. Surg vol. 73 :760–761 (Sep. 1986).

T. T. Liesegang et al "The use of Hydroxypropyl Methyl–Cellulose . . . " Am. J. of Opth. 102:723–726 (Dec. 1986).

A. Henrick et al "Organic Tissue Glue in the Closure of Cataract incisions" J. Cat. Ref. Surg vol. 13:551-53 (1987) (no month avail.).

S. R. Gundry et al "A quantitative and Qualitative comparison of Fibrin Glue Albumin——" J. Surg. Res. 43:75–77 (1987) (no month avail.).

M. P. Fried et al "Head ± Neck applications of the milliwat Laser" Lasers in surg ± Med. 7:46–50 (1987) (no month avail.).

J. E. Bailes et al "Review of Tissue Welding Application in Neurosurgery" Microsurgery 8;242–244 (1987) (no month avail.).

D. P. Poppas et al "Laser welding in Urethral surgery . . . "J. Uralogy vol. 139:415–417 (1987–88) (no month avail.).

D. Miller et al "Healon a guide to its use in Opthalmic surgery" pp. 5–28 (no date avail.).

D. F. Thompson et al "Fibrin Glue: A review of its Preparation, Efficacy and adverse effects——" Drug. Int. ±Clin. Pharm 22:946–95 (1988) (no month avail.).

A. F. S. Flemming et al "Laser assisted Microvascular Anastomosis——" Br. J. Plast Surg 41: 378–388 (1988) (no month avail).

B. A. Lowe et al "Vasovasostomy in the Murine Vas Deferens——" Lasers in Surg ± Med 8:377–380 (1988) (no month avail.).

G. E. Kopchock et al "co2 and Argon Laser Vascular Welding——" Laser in Surg ± Med 8:584–588 (1988) (no month avail.).

H. Zauberman et al "Use of Fibrin Glue in ocular Surgery" Opth. Surg vol. 19 No. 2: 132–133 (1988) (no month avail.).

Su Wang et al "Effect of blood bonding on Bursting Strength——" Microsurgery 9:10–13 (1988) (no month avail.).

S. Rochkind et al "Low-Energy Co2 Laser Intestinal Anastomosis——" Laser in Surg ± Med 8:579–583 (1988) (no month avail.).

R. A. White et al "Mechanism of Tissue Fusion in Argon Laser-welded——" Lasers in Surg ± Med 8:83–89 (1988) (no month avail.).

L. W. Murray et al "Cross-linking of extra cellular matrix Proteins——" Lasers in Surg. ± Med. 9:490–496 (1989) (no month avail.).

R. Moosdorf et al "Laser-Assisted Anastomosis of the Trachea——" V. Surg. pp. 51–58 (Jan./Feb. 1989).

J. S. Saver et al "the first sutureless, Laser-welded, end-to end Bowel/Anastomosis" Lasers in surg. ± Med. 9:70–73 (no month avail.).

P. T. O. Gilbert et al "Laser-Assisted Vasovasotomy" Lasers in Surg. ± Med. 9:42–44 (1989) (no month avail.).

I. K. Arenberg et al "Autologous Fibrin Glue and Sealant——"OT. surg vol. 101 No. 6:709–712 (1989) (no month avail.).

T. E. Emerson "Unique Features of Albumin; A brief review" Crit. Care Med. vol. 17 No. 7 :690–693 (1989) (no month avail.).

G. S. Ganesan et al "Urethral Reconstruction using the Carbon Dioxide Laser——" J. Urol. vol. 142; 1139–1141 (1989) (no month avail.).

L. S. Bass et al "Sutureless Microvascular Anastomosis using the Yag Laser——" Microsurgery 10:189–193 (1989) (no month avail.).

M. C. Oz et al "Tissue soldering by use of indocyanine green——" J. Vasc. Surg. 718–725 11:5 (May 1990) (no month avail.).

B. Jean et al "Target dyes in Ophthalmology Part I" Laser in light in Opth. vol. 3 No. 1 pp. 39–45 (1990) (no month avail.).

C. S. Kischkel et al "Target dyes in opthalmology Part II" Lasers in light in Opth. vol. 3 No. 1 pp. 47–52 (1990) (no month avail.).

TISSUE BONDING AND SEALING COMPOSITION AND METHOD OF USING THE SAME

This is a continuation-in-part of Ser. No. 07/560,069, filed Jul. 27, 1990, now U.S. Pat. No. 5,209,776.

FIELD OF THE INVENTION

The present invention is directed to a composition adapted to bond separated tissues together or to coat tissues or prosthetic materials to enhance strength and water tightness preferably upon the application of energy and particularly to a composition which is activated by a laser to form a strong, biologically compatible bond or coating.

BACKGROUND OF THE INVENTION

All surgical disciplines are concerned with the repair of damaged tissues and vessels. Damage can be the result of direct trauma to the body or as part of a surgical procedure in which there is a separation of normally continuous tissue such as in vein or artery anastomoses. Regardless of the cause, proper repair of the tissue or blood vessel is an essential step in the positive outcome of surgery.

The joining of separated tissues has principally been performed by suturing or stapling in which the skilled hands of the surgeon stitch or staple the separated tissues together. This procedure not only requires significant skill but also is a slow, tedious process, particularly if extensive repair is required.

Suturing suffers from several other drawbacks which have complicated surgical procedures. First, leaks often develop at the ends of the joined tissues which can require resuturing. In addition, suturing itself is a trauma to the tissue which can cause additional damage and extend the healing period. Further there are occurrences of inflammation in vicinity of the sutures which can result in late failure of a repair or anastomosis.

As a result, efforts have focused on overcoming the difficulties associated with suturing by the development of sutureless repairs using surgical adhesives or glues which adhere to tissue surfaces and form a bond therebetween.

The most common tissue adhesive is fibrin adhesive or glue typically containing a concentrate of fibrinogen and thrombin as disclosed in U.S. Pat. Nos. 4,362,567, 4,414,976 and 4,909,251 and Canadian Patent No. 1,168,982. The adhesives require mixing immediately prior to application and react in a manner similar to the last stages of the clotting cascade to form a fibrin clot. The clot effects hemostasis, a cessation of bleeding. By virtue of the physical properties of a blood clot, a small amount of tensile strength is present in the clot. Fibrin glue has been used in a variety of surgical procedures for its hemostatic properties, biocompatibility and as a modest reinforcement of the strength or more commonly the watertightness of a repair. (See, for example, Dennis F. Thompson et al., "Fibrin Glue: A Review of its Preparation, Efficacy and Adverse Effects as a Topical Hemostat", *Drug Intell. Clin. Pharm.* vol. 22, pp. 946–952 (1988); and Richard L. Burleson et al., "Fibrin Adherence to Biological Tissues", *J. Surg. Res.* vol. 25, pp. 523–539 (1978).

Fibrin adhesive, however, has significant drawbacks which has prevented its commercial use in the United States. First, in order to prepare commercial quantities of fibrin adhesive the components must be obtained from pooled human blood. There is therefore the possibility of infection from agents such as Hepatitis "B", HIV virus and others. Particularly in the United States, the threat of infection has outweighed the benefits of obtaining commercial quantities of fibrin adhesive. As a result, the production of fibrin adhesive has been limited to quantities obtained from a patient's own blood to reduce the risk of infection. (See, for example, Karl H. Siedentop et al., "Autologous Fibrin Tissue Adhesive", *Laryngoscope* vol. 95, pp. 1074–1076 (September, 1985); Gidon F. Gestring et al., "Autologous Fibrinogen for Tissue-Adhesion, Hemostasis and Embolization", *Vasc. Surg.* vol. 17 pp. 294–304 (1983) and D. Jackson Coleman et al., "A Biological Tissue Adhesive for Vitreoretinal Surgery", *Retina* vol. 8 no. 4, pp. 250–256 (1988). These autologous procedures make the use of fibrin adhesive costly and time consuming and therefore of limited value.

Second, fibrin glue preparations suffer from poor tensile strength. Third, fibrin glue requires time consuming mixing of multiple reagents immediately prior to application. Finally, once the reagents are mixed the glue polymerizes, and its removal disrupts the tissue on which it has been applied.

Non-biological materials have been tried as surgical adhesives in an effort to reduce the risk of infection over adhesives obtained from pooled blood. Isobutyl-2-cyanoacrylate has been applied to separated tissues and has formed a solid watertight seal shortly after contact with the tissue. Khalid J. Awan et al., "Use of Isobutyl-2- Cyanoacrylate Tissue Adhesive in the Repair of Conjunctional Fistula in Filtering Procedures for Glaucoma", *Annals of Ophth.* pp. 851–853 (August, 1974). However, such adhesives have been criticized because they are irritating to tissues and difficult to apply. Andrew Henrick et al., "Organic Tissue Glue in the Closure of Cataract Incisions", *J. CATARACT REFRACT. SURG.* vol. 13, pp. 551–553 (September, 1987).

Thus, surgical adhesives have not been successful in replacing the suture as the primary means of tissue and vessel repair.

Another approach to sutureless tissue repair is tissue welding. Tissue welding involves the bonding of tissues together using an energy source such as a laser beam. Several types of lasers have been found useful for tissue welding including Nd:YAG, $CO_2$, THC:YAG and Argon. Julian E. Bailes et al., "Review of Tissue Welding Applications in Neurosurgery", *Microsurgery* vol. 8, pp. 242–244 (1987); Rodney A. White et al., "Mechanism of Tissue Fusion in Argon Laser-Welded Vein-Artery Anastomoses", *Lasers in Surgery and Medicine* vol. 8, pp. 83–89 (1988); Lawrence S. Bass et al., "Sutureless Microvascular Anastomoses using the THC:YAG Laser: A Preliminary Report", *Microsurgery* vol. 10, pp. 189–193 (1989), Masame Suzuki et al., U.S. Pat. No. 4,625,724, Jude S. Sauer U.S. Pat. No. 4,633,870; Douglas Dew, U.S. Pat. Nos. 4,672,969 and 4,854,320, each incorporated herein by reference.

Tissue welding has been performed on a variety of tissues. For example, a carbon dioxide laser has been used in nerve tissue repair as described in Julian E. Bailes et al., *Microsurgery*. Tissue welding has successfully repaired intestinal tissue. Semion Rochkind et al., "Low-Energy $CO_2$ Laser Intestinal Anastomosis: An Experimental Study" *Lasers in Surgery and Medicine* vol. 8 pp. 579–583 (1988).

The use of lasers to directly weld tissues can eliminate about two-thirds of the time needed to repair damaged tissues or blood vessels. However, histological analysis of direct laser welds has shown transmural thermal injury at the site of the weld which adds to the trauma of the injury and surgery. In vascular anastomosis, this can lead to complicating aneurysm formation at the weld site which presents a threat to the healing process and in some cases may lead to internal bleeding and complications associated therewith. Further, the welds produced by direct laser contact have been characterized by marginal strength. The welds are prone to leakage and can burst in some cases.

To overcome the problems of direct tissue welding efforts have been made to employ organic agents which improve weld strength and at least minimize trauma to the tissue brought on by direct contact with laser energy. Typically, these agents known as laser adhesives or glues absorb laser energy forming a weld which bonds separated tissues together. In some cases, the laser adhesive selectively absorbs the laser energy thereby reducing the risk of transmural thermal injury. For example, blood has been used as a welding agent in laser repair surgery to improve bond strength and arterial healing through early fibrin cross-linking. Su Wan et al., "Effect of Blood Bonding on Bursting Strength of Laser-Assisted Microvascular Anastomoses", *Microsurgery* vol. 9, pp 10–13 (1988). Egg white albumin has also been used as a laser glue. Dix P. Poppas et al., "Laser Welding in Urethral Surgery: Improved Results with a Protein Solder", *J. Urology* vol. 139, pp. 415–417 (February, 1988) and George S. Ganesan et al., "Urethral Reconstruction Using The Carbon Dioxide Laser: An Experimental Evaluation", *J. Urology* vol. 142 pp. 1139–1141 (October, 1989).

Despite these efforts, laser adhesives still suffer from deficiencies which make their universal application problematical. In particular, laser adhesives are difficult to apply to separated tissues. They are either in the form of semi-solids (e.g. fibrinogen) or liquid (e.g. albumin or blood). As a semi-solid, the product must be cut into strips and placed at the weld site. Quite often the solid strip will move during application requiring time consuming repositioning. Additionally, the strip may shrink when exposed to the laser beam and weld only a portion of the tissue. The unwelded portion may be large enough to permit the passage of blood. This requires the use of additional strips of welding material and time consuming repeat operations.

Liquid laser adhesives are disadvantageous because they can run off of the weld site and thus may also require repeat applications. In addition, conventional laser adhesives made of protein materials, such as fibrinogen, often form rigid welds which reduce the flexibility of the welded tissues, particularly welded blood vessels. If the vessel is subjected to normal pressure fluctuations which occur during the cardiac cycle, such as the unclamping of the blood vessel or when the patient moves suddenly, the weld can rupture causing internal bleeding and related complications.

It therefore an object of the present invention to provide a composition which can form a strong, flexible biological compatible bond between separated tissues preferably upon the application of energy such as a laser beam.

It is another object of the invention to provide a composition which can form a watertight, flexible seal in tissues or prosthetic materials.

It is still another object of the invention to provide a laser adhesive whose viscosity can be modified according to the desired application to facilitate placement of the composition at the tissue site.

It is still another object of the invention to provide a method of bonding separated tissues or coating tissues to form a watertight seal using a composition which is easy to handle, particularly during surgical procedures.

It is still another object of the invention to provide methods of formulating the adhesive composition, packaging, and storing the same.

SUMMARY OF THE INVENTION

The present invention is directed to a composition suitable for bonding separated tissues and/or prosthetic materials together or for coating tissues or prosthetic materials, while maintaining sufficient flexibility to allow normal tissue or prosthetic function. The bonding or sealing of the separated tissues and/or prosthetic material can be enhanced by the application of energy and/or photons such as in the form of a laser beam. The composition may also be used to coat prosthetic materials to form a watertight or resistant seal.

The viscosity of the composition can be varied so that delivery, positioning, and stability during welding and final elasticity and strength are appropriate for the selected application. Such attributes allow faster, more efficient surgical repair of damaged or weakened tissues than is possible with suturing or known sutureless procedures.

The composition, preferably in the form of a solution, most preferably an aqueous solution comprises a first component which provides the tensile strength necessary to keep the welded tissue together, joining the separated tissue or providing a watertight, flexible seal on a tissue or prosthetic or implant surface. The second component forming part of the composition is adapted to support the first component producing an improved degree of inter-relationship among the molecules of the first component. By combining the components in this way bond strength is enhanced, making this composition a significant improvement over the prior art. The second component may also contribute sufficient elasticity to enable the weld to move in unison with the tissue or vessel during its normal bodily functions.

The second component may also function as a viscosity modifier according to the end use of the composition by raising or lowering the viscosity. Optionally, a viscosity modifier and/or bonding enhancer may be added to the composition according to need. The resulting composition provides a tissue adhesive having excellent strength and superior handling characteristics. The composition is particularly suited for laser welding by forming a strong, uniform, elastic weld or coating.

The first component is selected from natural or synthetic peptides enzymatically modified, cleaved, or shortened variants thereof and cross-linked derivatives thereof and mixtures thereof. Included among the peptides are simple proteins, conjugated proteins, and mixtures thereof. Examples of such proteins include globular proteins and fibrous or structural proteins, and mixtures thereof.

Examples of globular proteins include synthetic or natural serum proteins, natural or synthetic derivatives thereof, salts, enzymatically, chemically, or otherwise modified, cleaved, shortened or cross-linked, oxidized or hydrolyzed derivatives or subunits thereof, and mixtures thereof. Examples of fibrous or structural proteins include synthetic or natural collagen, elastin, keratin, fibroin, fibrin, and fibronectin, natural or synthetic derivatives thereof, salts, enzymatically, chemically or otherwise modified, cleaved, shortened or cross-linked, oxidized or hydrolyzed derivatives or subunits thereof, and mixtures thereof. Examples of serum proteins are albumin, α-globulins, β-globulins, γ-globulins, transthyretin, fibrinogen, and thrombin. Other globular and fibrous proteins as would be obvious to one skilled in the art may also be used.

The second component is generally selected from compounds which support the first component such as by forming a matrix or gel or sol with the first component. These compounds are generally selected from natural or synthetic proteoglycans, glycoproteins, saccharides, polyalcohols, protein gels, gelatins, natural or synthetic derivatives thereof, enzymatically, chemically or otherwise modified, cleaved or shortened variants, salts, cross-linked, oxidized or hydrolyzed derivatives or subunits thereof of all of the above, and mixtures thereof.

The proteoglycans are preferably natural or synthetic non-cellular body matrix materials found in the interstices between cells. Such materials are typically glycosaminoglycans and include hyaluronic acid, salts of hyaluronic acid including sodium hyaluronate, chondroitin sulfate, dermatan sulfate, keratan sulfate, heparin, and heparan sulfate. The saccharides are preferably selected from oligosaccharides such as fructose, and polysaccharides such as cellulose compounds, dextrans agarose, alginic acid and pectins. Examples of the cellulose compounds include hydroxypropylmethylcellulose, hydroxycellulose, methylcellulose, carboxymethylcellulose, and hydroxyethylcellulose. The polyalcohols are preferably selected from glycerin, mannitol, sorbitol, polyvinyl alcohol, and polyethylene glycol. Other second component materials from these classes of compounds as would be obvious to one skilled in the art may also be employed.

The composition is prepared in a form ranging from a flowable liquid to a sol to a viscous gel depending upon the application and the concentration of components. For example, the composition is preferably employed in the form of a viscous gel for bonding of separated tissues. On the other hand, the formation of a watertight or resistant seal on tissues or prosthetic materials is most efficiently accomplished using a less viscous composition.

In some cases the combination of the peptide and support material will spontaneously form a weld. In other cases, it may be necessary to activate the composition, with energy and/or photons. In general, activation with energy and/or photons rapidly accelerates the bonding process. The energy and/or photons employed in the present invention must be capable of activating the composition in a manner which produces the desired bonding or coating characteristics.

The composition can be activated through the application of energy and/or photons. The energy preferably has a wavelength in the electromagnetic spectrum, and is selected from X-rays, ultraviolet light, visible light, infrared light, and radiowaves. Thermal energy delivered through direct contact as for example with a probe heated electrically such as an electrocautery, or a probe heated through gas compression in the tip, or the passage of heated gas or liquid through the tip, may be used. Sound energy in the ultrasonic frequency, or radiowaves in the microwave range may be employed. The energy can be delivered in a continuous or noncontinuous fashion, in a narrow or broad band of electromagnetic wavelengths. Examples of photon sources include monochromatic and polychromatic light, coherent or noncoherent light, delivered in a continuous or noncontinuous fashion. Examples of noncontinuous energy and/or photon delivery include single and/or multiple pulse train delivery. Photons can be delivered in a polarized or nonpolarized fashion, direct or reflected, with or without internal or external interference.

Most preferable are the use of lasers including, but not limited to, those in the ultraviolet, visible, or infrared range. In particular, the THC:YAG (2150 $\mu$m), Nd:YAG (1064, 1320 nm), KTP (532 $\mu$m), Dye (577, 590, 610 nm), Krypton (647 nm), Argon (488 and 514 nm), Carbon dioxide (10,600 nm), Diode (810 nm), Excimer (193, 222, 249, 308, 351 nm) lasers are preferred.

The composition of the present invention can additionally contain viscosity modifiers and/or bonding enhancers in accordance with the end use of the composition. For example, the addition of viscosity modifiers provides a composition with a viscosity particularly suited to tissues which are to be repaired or sealed. A composition having a high viscosity is preferably employed to bond separated tissues while lower viscosity compositions are best suited to form a coating for watertight sealing of continuous tissue masses and prosthetic materials such as Gortex TM vascular grafts and the like. Such viscosity modifiers include compounds previously mentioned which are non-cellular body matrix materials such as hyaluronic acid and salts thereof such as sodium hyaluronate, or sodium chondroitin, or saccharides such as fructose, hydroxypropylmethylcellulose, hydroxyethylcellulose, carboxymethylcellulose, hydroxymethylcellulose, dextrans, agarose, alginic acid or pectins, or polyalcohols such as glycerine, or protein gels such as collagen, and caseinates, and mixtures thereof.

Bonding enhancers may also be used to improve the bonding strength of the composition. Certain second component materials may be selected for this purpose, and/or bond enhancers may be added to the composition as a third component. These are generally selected from polar compounds such as charged glycosaminoglycans, oligosaccharides and polysaccharides, polyalcohols, and polar dyes. Examples of these polar compounds include hyaluronic acid, chondroitin sulfate, carboxymethylcellulose, hydroxymethylcellulose, glycerine, indocyanine green, and fluorescein sodium. Polyvalent cations, such as calcium, may also serve this purpose by binding to the negatively charged moieties in the proteins, such as albumin, and the glycosaminoglycans such as hyaluronic acid and chondroitin sulfate.

The use of mucoadhesives as second component materials and/or as a third component bond enhancer, is advantageous on mucin containing surfaces, such as the gastrointestinal tract, and the pulmonary system. Examples of mucoadhesives include carboxymethylcellulose and sodium alginate. Use of these materials on other surfaces, such as those with a high collagen content, which have a large concentration of hydroxyl groups, such as that imparted to the collagen through 4-hydroxyproline, may also be advantageous in facilitating bond formation. It is believed the mucoadhesive molecules tend to attach to mucin through the entanglement of the polymer chains with mucin on the surface of the tissue, and unionized carboxylic acid groups and hydroxyl groups on the polymer may form hydrogen bonds to the mucin or other molecules on the collagen. It is believed that a high charge density is preferred for both swelling and hydrogen bonding for firm attachment to occur. (See J. R. Robinson et al.: Bioadhesive Polymers for Controlled Drug Delivery. *Ann. NY Acad. Sci.* 507:307-314, 1987, incorporated herein by reference.) Use of these materials as part of the present invention, therefore should be advantageous to facilitate the bonding of the composition to the desired tissue surface. Other mucoadhesives as would be obvious to one skilled in the art may also be employed.

The composition may additionally contain as needed pH modifiers, surfactants, antioxidants, osmotic agents, and preservatives.

The components of the composition are combined together in quantities which provide a desired bonding strength as well as a viscosity which is particularly adapted to the end use. In general, the amount of the peptide is in the range of from about 1 to 70% by weight, preferably about 8 to 35% by weight. The amount of support material varies depending on the support material chosen. Saccharides are typically employed in the range of from about 0.1 to 70% by weight. The amount of the glycosaminoglycans is preferably from about 0.1 to 20% by weight. Polyalcohols may be employed in an amount of from about 0.1 to 90% by weight. Protein gels and gelatins may be employed as second component materials in an amount of from about 5 to 80% by weight.

The amount of additives such as viscosity modifiers and bonding enhancers is generally no more than about 65% by weight.

The viscosity of the composition is chosen in accordance with the particular surgical procedure being performed. For bonding of separated tissues, a viscosity of from about 1,000 to 1,000,000 centipoise is advantageously employed, preferably in the range of from about 20,000 to 200,000 centipoise. A composition having a viscosity in the preferred range can be easily placed on the separated tissues by ejecting through a hypodermic syringe and spread out by moving the syringe tip. In this viscosity range, the composition does not run off the tissues and remains fixed even when energy is applied to form the tissue weld.

The composition preferably has a lower viscosity for applications requiring the formation of a watertight coating for sealing tissues or prosthetic materials. The preferred viscosity for coating is in the range of from 10 to 1,000 centipoise. The lower viscosity is preferred because the composition should be readily spreadable to efficiently cover the tissue or material to be coated.

In compositions containing hyaluronic acid, or other non-Newtonian fluids, the viscosity decreases with increasing shear forces. Accordingly, the viscosity of the composition can be modulated by altering the shear forces present when the composition is applied to the surface. As an example, a composition which is very thick when it is stationary can be injected through a graft at a rapid or high sheer rate to reduce its viscosity during the transit phase in which the graft is coated with the material.

This property known as psuedoplasticity is also characteristic of blood. It is ideal for welding at sites that are not subject to shearing forces during the welding process. When the composition is being injected, shear forces are high, and the viscosity decreases. This allows for easy injection. After being deposited on the tissue, the shear forces drop to zero, and the viscosity of the composition increases correspondingly. As a result, the composition stays localized on the tissue in the area to be welded.

The composition of the present invention provides a tissue bond having high tensile strength, elasticity, deformability, water tightness, viscosity and adhesivity for a large variety of surgical procedures. The composition can also be used to coat implantable devices to enhance their strength and resistance to fluids, to seal pores in the weave of the material, and reduce thrombogenicity. The composition is easily reproducible, non-infectious and stays stable and therefore can be used with greater speed and reliability than known surgical adhesives.

DETAILED DESCRIPTION OF THE INVENTION

The composition of the present invention can be used to bond separated tissues together and to coat continuous tissue masses or prosthetic materials to enhance their strength and/or make them impermeable to fluids. The coating applications of the invention make it possible to reinforce a weakened tissue such as an arterial wall.

The preferred proteins used in the present invention are structural proteins such as collagen and serum proteins such as albumin. Although fibrinogen and fibrin are not presently preferred embodiments due to the risk of infection and stability problems, should these problems be overcome by new production and/or purification techniques, fibrinogen and fibrin would become preferred embodiments of the present invention particularly in combination with albumin.

Collagen is the most abundant protein in the body. There are five types of collagen, each containing three polypeptides of about 1,000 residues per chain. The main function of collagen is to maintain the shape and to resist the deformation of the tissues. In a similar fashion, the ropelike collagen fibrils help to enhance bond strength and to resist deformation in the tissue bonding or sealing composition of the present invention.

Another advantage of collagen is that when collagen is heated it can be denatured, and solubilized for easy application as a gelatin-like solution. When cooled, the collagen is partially renatured, resulting in a gel formation with excellent tensile strength. Heated collagen, therefore, is an ideal protein component in the present tissue bonding or sealing composition. Through heating, collagen can be solubilized and easily injected or applied, and by cooling it can be turned into a gel which provides both tensile strength and flexibility to the bond. Collagen can also be rendered in a sterile form. Moreover, collagen is more stable than its fibrin counterpart, both on the shelf and in vitro and collagen does not expose the recipient to the risk of infection as does fibrin glue.

Albumin, when used in the present composition, provides distinct advantages over current procedures using "biological glues" which employ fibrin obtained from pooled blood samples. This exposes the recipient to the risk of infections from AIDS, Hepatitis A, Hepatitis non A and non B, Cytomegalovirus, Jakob-Creutzfeld disease, and others. The present composition containing human albumin on the other hand, while obtained from pooled blood products, does not expose the patient to these risks. Human albumin, unlike human fibrin, can be subjected to ultrafiltration techniques which results in a high yield of albumin free of infectious agents. Moreover, human albumin is more stable than its fibrin counterpart, both on the shelf and in vivo. This is because fibrin can be activated by thrombin and calcium, which are both present in the blood and other body tissues. Moreover, after its use, plasma fibrinolytic activity immediately begins to degrade the fibrin glue. As there is no enzyme system specifically designed to degrade albumin, its absorption will be slower than that of the fibrin glue counterpart. On the shelf, albumin is also more stable than fibrin glue.

Albumin is a transport protein with a molecular weight of 66,500 Daltons, and a half life of 15-20 days. It accounts for 70-80% of the colloid osmotic pressure of the plasma, and is distributed throughout the extracellular water. More than 60% of human albumin is located in the extravascular fluid compartments. It is, therefore, ideally suited for welding as it is present in most of the tissues which are to be welded, and will not cause a tissue inflammatory response. Moreover, its half-life exceeds the time period necessary for wound strength to reach a level sufficient to resist normal stresses.

The preferred polysaccharides have a high molecular weight and form long chain molecules which produce viscous, gel-like materials at low concentrations. Additionally, the presence of multiple charged or uncharged side chains may be advantageous to facilitate gel formation, production of a high viscosity composition, and/or interaction between molecules in the composition and/or tissue. Low molecular weight, small chain polysaccharides require higher concentrations to produce viscous, gel-like materials, and tend to be less desirable. One of the preferred polysaccharides is hydroxypropylmethylcellulose which is preferably used in a sterile aqueous solution. As a sterile solution it may be formulated to have a molecular weight exceeding 80,000 daltons and a viscosity of at least about 4,000 centipoise. See, for example, Thomas J. Liesegang et al., "The Use of Hydroxypropyl Methyl Cellulose in Extracapsular Cataract Extraction with Intraocular Lens Implantation", *Am. J. Ophth.* vol. 102, pp 723-726 (December, 1986).

Another preferred polysaccharide is carboxymethylcellulose, which is also preferably used in a sterile aqueous solution. As a sterile solution it may be formulated in a 1% aqueous solution to have a viscosity of 10-3,000 centipoise or higher depending on its molecular weight. For example, a 2% aqueous solution of 45,000 Dalton's has a viscosity of 10-20 centipoise, a 2% solution of 100,000 Dalton's has a viscosity of 400-800 centipoise, and a 1% aqueous solution of 200,000 Dalton's has a viscosity of 1500-3000 centipoise.

Another preferred polysaccharide is alginic acid, which is also preferably use in a sterile aqueous solution. As a sterile solution it can be formulated into a 2% solution having a viscosity of 250 to 14,000 centipoise or higher, depending on its molecular weight. For example, a 2% solution of alginic acid weighing 200,000 Dalton's has a viscosity of 14,000 centipoise, a 2% solution of alginic acid weighing 150,000 Dalton's has a viscosity of 3,500 and a 2% solution of alginic acid weighing 100,000 Dalton's has a viscosity of 250 centipoise. Pectin is another preferred saccharide, which can be formulated into an aqueous solution.

The preferred group of compounds under the general class of proteoglycans and derivatives thereof have a high molecular weight and form long chain molecules which produce viscous, gel-like materials at low concentrations. In particular, glycosaminoglycans which include hyaluronic acid and salts thereof, particularly sodium hyaluronate and chondroitin sulfate, are preferred.

Hyaluronic acid is a polymer centered in the extracellular matrix of animals and humans. It is thought to form the filamentous backbone of both cartilage and other connective tissues.

Hyaluronic acid has a molecular weight of 4 to $80 \times 10^6$ Daltons. Structurally, hyaluronic acid is characterized by repeating disaccharide subunits of sodium glucuronate linked to an N-acetylglucosamine molecule by a $\beta 1 \rightarrow 3$ glucosidic bond. The disaccharide units are linked together with $\beta 1 \rightarrow 4$ glucosidic bond to form large polymers. Each subunit has one negative charge, which may help to explain its bond strength enhancing affect. (See *Principles of Biochemistry: Mammalian Biochemistry*, 7th edition, edited by Emil Smith et al., pp. 7 and 229 (1983).

Hyaluronic acid and its salts have other advantages. In its purified form, sodium hyaluronate has a viscosity of 40,000 centipoise at a shear rate of 2 sec.$^{-1}$ at 25° C., and over 200,000 centipoise at a shear rate of zero. This non-Newtonian, or pseudoplastic viscous property of hyaluronic acid makes it ideal for tissue welding. At high shear rates, such as occurs during injection through a syringe or long cannula, the viscosity of hyaluronic acid is low, facilitating injection. This allows for its easy application to tissues. At low shear rates, such as after application to tissues, its viscosity is high. This helps to keep it localized to the tissue in the area to be welded or sealed. Healon, Chapter 1, Balazs EA., "Sodium Hyaluronate and Viscosurgery" *Healon* By David Miller and Robert Stegmann, John Wiley & Sons, New York, (1983).

Therefore, hyaluronic acid is ideally suited for tissue welding for two reasons. First, it helps to increase the tissue adhesive strength by providing a backbone for the protein component of the tissue adhesive material. Second, the pseudoplastic properties of hyaluronic acid provide it with ideal handling characteristics.

Chondroitin sulfate is a polymer centered in the extracellular matrix of animals and humans. It has a molecular weight of 22,500 daltons, and is composed of a repeating disaccharide subunit of glucuronic acid in $\beta 1 \rightarrow 3$ linkage with N-Acetylgalactosamine. The subunits are then combined by $\beta 1 \rightarrow 4$ linkage to form large polymers. Unlike hyaluronic acid, chondroitin sulfate contains a double negative charge per repeating disaccharide unit, which may enhance bond strength in certain instances. This may help in the bonding and sealing of corneal tissue, which has the highest natural concentration of chondroitin sulfate of any tissue in the body.

Chondroitin sulfate, like hyaluronic acid, is highly viscous in concentrations of 50 mg/ml, where its viscosity is 4000 centipoise (at shear rate of 2 sec$^{-1}$, 25° C.). However, unlike hyaluronic acid, chondroitin sulfate is a Newtonian fluid, and does not change viscosity with changing shear rates. This property will allow it to remain localized more readily in areas where there are large shear forces during bonding.

For control of the compositions handling characteristics, the use of long chain molecules, particularly saccharides, and proteoglycans, is advantageous. As the concentration of these molecules, or their molecular weight at a fixed concentration, is increased, higher viscosity and gel-like materials tend to be produced. (See E. L. Smith et al., "Connective Tissue, Collagen, Elastin, Proteoglycans, Fibrinectin Principles of Biochemistry, Mammalian Biochemistry" (Chapter 6, 7th Edition. McGraw-Hill, pp. 211-242, 1983 incorporated herein by reference)). As the concentration of these molecules, or their molecular weight at a fixed concentration, is decreased, lower viscosity, more watery materials tend to be produced. Therefore, through modification of the long chain molecule's molecular weight and/or concentration, the handling characteristics of the composition can be controlled to suit the desired application.

Compositions in which thicker, more viscous handling characteristics are desirable can be formulated by increasing the molecular weight and/or concentration of the second component. Whereas those in which a thin, liquid, watery formulation is desirable can be formulated by decreasing the molecular weight and/or concentration of the second component.

The composition of the present invention may also include indogenous or exogenous chromophores to facilitate visualization of the material during placement into warm blooded animals. Use of a chromophore will allow material which becomes displaced from the desired application site to be easily visualized, and subsequently removed using a cellulose sponge, gauze pad, or other absorbing material. The use of endogenous chromophores, such as hemoglobin, is disclosed in Krueger R, Almquist E: Argon laser coagulation of blood for anastomosis of small vessels. *Lasers Surg. Med.* 5:55-60, January, 1985. Use of exogenous chromophores for aid in the placement of biological glues has been previously described (see I. Nasaduke, et al. "The use of Autogenous Rabbit Fibrin Sealant to Plug Retinal Holes in Experimental Detachments". *Ann. Ophth.* 18:324-327, 1986), incorporated herein by reference. Chromophores that may be used, include, but are not limited to fluorescein isothiocyanate, indocyanine green, silver compounds such as silver nitrate, rose bengal, nile blue and Evans Blue, Q-Switch TM, a dye made by Kodak, Inc., Sudan III, Sudan Black B and India Ink. The chromophores are preferably present in a concentration of from about 0.01 to 50% by weight based on the total weight of the composition. Other chromophores as would be obvious to one skilled in the art may also be employed.

The present invention may also include substances which alter absorption characteristics of the composition so that the composition absorbs energy at low energy levels. This enables the heating of the material using certain wavelengths of the electromagnetic spectrum which are selectively absorbed by the energy absorbing compound. For example, this would allow heating of the material using certain lasers whose energy would otherwise not be absorbed by the composition of the present invention, and allows the composition to be welded to the target using these lasers. These substances reduce possible collateral damage to adjacent tissues typically associated with high energy level activators such as laser beams. See, "Mehmet C. Oz et al., "Tissue Soldering by Use of Indocyanine Green Dye-enhanced Fibrinogen with the Near Infrared Diode Laser", *J. Vasc. Surg.* vol. 11 no. 5 pp. 718-725 (May, 1990); and B. Jean et al., "Target Dyes in Ophthalmology—Parts I and II", *Lasers and Light in Ophthalmology* vol. 3 no. 1, pp 39-52 (1990). Exogenous dyes such as indocyanine green, fluorescein and endogenous chromophores such as hemoglobin and melanin and the like are particularly suited for this purpose. These dyes also may increase adhesivity, weld strength and viscosity. The dyes are preferably present in the composition in an amount of from about 0.01 to 50% by weight based on the total weight of the composition.

The addition of such dyes which have a peak light absorption at a specific wavelength, allows for the selective activation of the composition at the site of the weld or coating, while substantially reducing the risk of undesirable collateral thermal damage to adjacent tissues. By selecting a wavelength of light, emitted from a light source such as a laser beam, which matches the peak absorption wavelength of the dye used, a lower threshold of input energy is needed to obtain the desired tissue effect. This lower energy has little effect on untreated tissue. Thus, the energy is targeted only where the dye is applied or incorporated. As an example, indocyanine green is a dye that selectively binds to human or animal albumin and has a maximum absorbance at 805 nm in an albumin solution. When the dye is mixed with albumin, continuous wave diode laser light, which is commercially available at 808 nm wavelength, can be selectively used to heat and coagulate the albumin. The selection of the peptide used as the first component is affected by the laser-dye combination desired. Peak absorption for indocyanine green in water solution is 770 nm. This does not match the output of the diode laser. The 805 nm peak is obtained in albumin solution but not in solution with other proteins, such as fibrinogen. This effect is observed independent of albumin absorption which is low at 805 nm.

Other dye-laser combinations, include, but are not limited to, fluorescein isothiocyanate (Absorbance 490 nm) and an argon laser operating at 488-514 nm; silver compounds such a silver nitrate and a krypton laser (676 nm); dye compounds such as rose bengal, nile blue and Evans blue and Dye lasers absorbing in the range of 200 to 610 nm. Q-switch II TM a dye obtained from Kodak, absorbs light from a Nd:YAG laser at 1064 nm and 1320 nm. Sudan III, Sudan black B and India Ink may also be utilized to selectively adsorb light from any of the above-mentioned lasers.

The compositions may additionally contain as needed pH modifiers, surfactants, antioxidants, osmotic agents, and preservatives. Examples of pH modifiers include acetic acid, boric acid, hydrochloric acid, sodium acetate, sodium bisulfate, sodium borate, sodium carbonate, sodium citrate, sodium hydroxide, sodium nitrate, sodium phosphate, sodium sulfite, and sulfuric acid. Examples of surfactants include benzalkonium chloride. Examples of antioxidants include bisulfates. Examples of osmotic agents include sodium chloride. Examples of preservatives include chlorobutanol, sorbate, benzalkonium chloride, thimerosal, methylparaben, propylparaben, Ethylenediaminetetraacetic acid (EDTA), and polyquad.

Typically the pH modifiers, surfactants, antioxidants, osmotic agents, and preservatives are present in a concentration of from about 0.001 to 5% by weight.

The method of formulating the composition of the present invention may be performed in a number of ways, including, but not limited to the following preparation techniques, which generally result in a well formulated composition. The preparation is generally performed at 25°-30° C. or cooler for globular proteins, and may be performed at temperatures of from 25°-200° C. or higher, preferably 25°-100° C. for collagen, and other fibrous proteins.

Initially, the first and second components are formulated into sterile aqueous solutions at the desired concentration. When the first or second component is anhydrous, lyophilized, or partially hydrolyzed, they are hydrated to the desired concentration with sterile water or a sterile aqueous solution containing chromophores, electrolytes, pH modifiers, surfactants, antioxidants, osmotic agents, and preservatives. During the hydration process, external agitation by shaking or vibrating the container, or internal agitation by stirring the composition using a spatula or other object which is inserted into the container, are advantageous. Additional hydration of the first and second component may be achieved after the components are combined.

Second, after hydration to the desire concentration, the first and second components are combined in a ratio which is determined by the desired end use of the composition. To achieve the desired improved degree of interrelationship among the molecules of the first component, it is generally advantageous to agitate the composition either internally, or externally as described in the first step. Generally, the material is mixed for 5 or more minutes, or until a homogenous solution, gel or sol is formed. The material may additionally be cooled to from 5°–20° C. to aid in sol or gel formation.

Third, after mixing, additional material can be added to increase the viscosity of the material, the bond strength of the material, to enhance the visualization of the material. Other agents, such as pH modifiers, surfactants, antioxidants, osmotic agents, and preservatives may be added at this time.

Finally, the product of the third step is then packaged and stored in one of a number of ways. For example: (1) The materials can be placed in an aqueous form into a sterile syringe, or vial; and (2) the materials can be dehydrated, as for example through lyophilization, and stored in an anhydrous or partially hydrated state. For materials containing chromophores, or other photon or energy absorbing components, dark, pigmented containers are preferred to prevent light activation or decay of the composition. When formulated as an aqueous solution, refrigeration of the product at 4°–10° C. is generally preferred.

EXAMPLE 1

0.55 ml of a 25% solution of human albumin obtained from the New York Blood Center was combined with 0.55 ml of hyaluronic acid and 5.5 mg of a sterile indocyanine green dye (Cardio-Green TM obtained from Becton-Dickinson). The resulting product was placed on corneosclera tissue as described below and exposed to a pulsed THC:YAG laser having a wave length of 2.15 μm at an input level of 106 Joules and a pulse rate of 4 pulses per second.

The resulting weld was tested for normal preglue leaking pressure and post weld strength as follows.

Freshly enucleated porcine eyes were used to determine the strength of the bonding in closing corneoscleral cataract incisions similar to those used in cataract extraction surgery. A 64 beaver blade was used to make a 5–10 mm partial thickness scleral incision, 1–3 mm posterior to the limbus. The incision was extended anteriorly into clear cornea, and a superblade was used to enter the anterior chamber. A 25 G butterfly needle was inserted into the anterior chamber through clear cornea, and was attached to a water column of Dextrose 5% Normal Saline solution.

The water column was elevated until leakage was noted at the wound margin. The process was repeated at least three times until reproducible-results were obtained. The glue was then applied and congealed with the laser to form a firm seal. The water column was then elevated until leakage could be visualized around the glue margin, which is reported as the bursting pressure. If the bursting pressure was near the baseline values, additional glue was applied to the area of leakage, and additional laser energy was applied. If this resulted in a strong bond, this value was reported as the bursting pressure.

The results are shown in Table 1. It will be noted that viscosity was measured subjectively on a scale of 1–10 wherein a viscosity of 1 was characterized by a flowable liquid such as water, a viscosity of 5–8 is similar to honey and a viscosity of 10 was characteristic of a gel-like substance.

TABLE 1

| | |
|---|---|
| Hyaluronic Acid 10 mg/ml | 0.55 ml |
| 25% Human Albumin | 0.55 ml |
| Indocyanine green dye | 5.5 mg |
| Incision Length | 9 mm |
| Distance from limbus | 2 mm |
| Normal Pre-Glue Bursting pressure | 4 in. $H_2O$ |
| Post-Welding Bursting pressure | 60 in. $H_2O$ |
| Viscosity | 7 |

EXAMPLE 2

The same composition was prepared as in Example 1 except that the indocyanine green dye was omitted. The sample was placed on tissue specimens and activated as described in Example 1. The results are shown in Table 2.

TABLE 2

| | |
|---|---|
| Hyaluronic Acid 10 mg/ml | 0.75 ml |
| 25% Human Albumin | 0.75 ml |
| Incision Length | 9 mm |
| Distance from limbus | 2 mm |
| Normal Pre-Glue Bursting pressure | 4 in. $H_2O$ |
| Post Welding Bursting pressure | >60 in. $H_2O$ |
| Viscosity | 7 |

EXAMPLE 3–9

Seven samples of the composition of the present invention were prepared by combining sodium hyaluronate (Healon TM manufactured by Pharmacia Inc. and Amvisc Plus TM manufactured by Med Chem Products, Inc.) and a mixture of 25% human albumin which contained 10 mg/ml of indocyanine green dye. The mixtures were refrigerated overnight to allow for adequate mixing.

The mixtures were applied to tissues in the same manner as described in Example 1 and exposed to laser light from a diode laser manufactured by Spectra-Physics, at a wavelength of 808 nm with an energy output of 300–450 milliwatts and a power density of 12 watts/cm$^2$ and a spot size of 2 mm.

On application of the laser energy an area of whitening occurred, followed by shrinkage, and then congealed. After adequate laser application, the glue set in a fashion similar to that seen with commercially available rubber cement. The elastic properties of the glue could be modulated by additional laser energy. As more energy was applied, firmer, less flexible, stronger bonds could be formed. At lower energy levels, the bond was more elastic. Over time, when allowed to dry further, both types of bonds appeared to become stronger.

However, total drying results in a brittle, friable material and is undesirable.

The samples were tested as described in connection with Example 1 and the results are shown in Table 3.

TABLE 3

| SAMPLE | HEALON (PARTS) | 25% HUMAN ALBUMIN WITH 10 MG/ML OF ICG DYE (PARTS) | INCISION LENGTH (MM) | DISTANCE FROM LIMBUS (MM) | NORMAL PRE-GLUE BURSTING PRESSURE (INCHES H$_2$O) | POST-WELDING BURSTING PRESSURE (INCHES H$_2$O) | VISCOSITY |
|---|---|---|---|---|---|---|---|
| 3 | 10 | 1 | 9 | 2 | 2 | 4 | 10 |
| 4 | 5 | 1 | 8 | 2 | 2 | 16 | 10 |
| 5 | 2 | 1 | 9 | 2 | 4 | 52 | 8 |
| 6 | 1 | 1 | 10 | 2 | 2 | 40 | 7 |
| 7 | 1 | 2 | 10 | 2 | 2 | 10 | 6 |
| 8 | 1 | 5 | 9 | 2 | 6 | 30 | 2 |
| 9 | 1 | 10 | 9 | 2.5 | 4 | 10 | 1 |

To determine if the low dye concentration in sample 3 was responsible for its lower bond strength, a dye concentration similar to that in sample 9 was made. 0.55 ml Healon TM was mixed with 25% albumin (0.051 ml) and 5.0 mg of indocyanine green dye. In this example the higher concentration of dye was not found to improve the strength of the bond formed with a 10 parts Healon TM to 1 part 25% human albumin with 10 mg/ml of indocyanine green dye mixture, indicating that the low dye concentration in sample 3 was not responsible for the lower bond strength. It is believed that the high Healon TM to albumin ratio in sample 3 was responsible for its lower tensile strength.

EXAMPLE 10

0.8 ml of Amvisc Plus TM (1.6% Sodium Hyaluronate), 0.8 ml of 25% human albumin and 0.2 ml of a 2.5 mg/ml sterile solution of Cardio-Green TM were mixed and then applied to tissues and exposed to laser energy in the same manner as described in Examples 3-9. The results are shown in Table 4.

TABLE 4

| | |
|---|---|
| AmviscPlus TM | 1 part |
| 25% Human Albumin | 1 part |
| Incision Length | 6 mm |
| Distance from limbus | 2.5 mm |
| Normal Pre-Glue Bursting pressure | 4 in. H$_2$O |
| Post-Welding Bursting pressure | 41 in. H$_2$O |
| Viscosity | 7 |

EXAMPLE 11

A mixture of 0.5 ml of a 2% hydroxypropylmethylcellulose solution (Occucoat TM manufactured by Lederle Laboratories), 0.5 ml of 25% human albumin and 0.1 ml of a 2.5 mg/ml sterile solution of Cardio Green TM was tested and exposed to laser energy in the same manner as in Examples 3-9. The results are shown in Table 5.

TABLE 5

| | |
|---|---|
| Occucoat TM | 1 part |
| Albumin | 1 part |
| Incision Length | 7 mm |
| Distance from limbus | 2 mm |
| Normal Pre-Glue Bursting pressure | 8 in. H$_2$O |
| Post-Welding Bursting pressure | 32 in. H$_2$O |
| Viscosity | 2 |

EXAMPLES 12-14

Three samples of the composition of the present invention containing the components and amounts identified in Table 6 were tested and exposed to laser energy in the same manner as described in Examples 3-9. The results are shown in Table 6.

TABLE 6

| SAMPLE | VISCOAT (PARTS) | 25% HUMAN ALBUMIN WITH 10 MG/ML OF ICG DYE | INCISION LENGTH (MM) | DISTANCE FROM LIMBUS (MM) | NORMAL PRE-GLUE BURSTING PRESSURE (INCHES H$_2$O) | POST-WELDING BURSTING PRESSURE INCHES (H$_2$O) | VISCOSITY |
|---|---|---|---|---|---|---|---|
| 12 | 1 | 1 | 7 | 3.0 | 6 | 13 | 8 |

| SAMPLE | HONEY (PARTS) | 25% HUMAN ALBUMIN WITH 10 MG/ML OF ICG DYE (PARTS) | INCISION LENGTH (MM) | DISTANCE FROM LIMBUS (MM) | NORMAL PRE-GLUE BURSTING PRESSURE (INCHES H$_2$O) | POST-WELDING BURSTING PRESSURE INCHES (H$_2$O) | VISCOSITY |
|---|---|---|---|---|---|---|---|
| 13 | 1 | 1 | 7 | 3.0 | 4 | 20 | 3 |

| SAMPLE | 15% DEXTRAN SOLUTION (PARTS) | 25% HUMAN ALBUMIN WITH 10 MG/ML OF ICG DYE (PARTS) | INCISION LENGTH (MM) | DISTANCE FROM LIMBUS (MM) | NORMAL PRE-GLUE BURSTING PRESSURE (INCHES H$_2$O) | POST-WELDING BURSTING PRESSURE INCHES (H$_2$O) | VISCOSITY |
|---|---|---|---|---|---|---|---|
| 14 | 1 | 1 | 10 | 2.5 | 4 | 40 | 3 |

EXAMPLE 15

2.0 ml of synthetic glycerine (manufactured by HUMCO Labs) was combined with one ml of a mixture of 25% human albumin solution containing a sterile solution of Cardio-Green TM in a concentration of 10 mg/ml. The sample was tested and exposed to laser energy in the same manner as described in Examples 3-9. The results are shown in Table 7.

TABLE 7

| | |
|---|---|
| Glycerine | 2 parts |
| 25% Human Albumin with 10 mg/ml of ICG dye | 1 part |
| Incision Length | 9 mm |
| Distance from limbus | 2 mm |
| Normal Pre-Glue Bursting pressure | 22 in. H$_2$O |
| Post-Welding Bursting pressure | 32 in. H$_2$O |
| Viscosity | 3 |

EXAMPLES 16-20

Freshly harvested rat skin was trimmed into strips and the edges of two strips brought into approximation. The adhesive mixtures shown in Table 8 were then topically applied. Energy was input until tissue soldering was effected to produce a weld of about 1 mm. Immediately after completion of the repair, weld length and break point (in grams) was measured. Samples 16-18 and control samples A, C and D were exposed to the same laser and under the same conditions described in connection with Examples 3-9. Control sample B and samples 19 and 20 were exposed to high frequency electrical diathermy (13.5 MHz electrocautery). The results are shown in Table 8.

TABLE 8

| SAMPLE | COMPOSITION | MEAN TENSILE STRENGTH (G/CM$^2$) |
|---|---|---|
| CONTROL A) | indocyanine green 0.5% | <100 |
| CONTROL B) | none | <100 |
| CONTROL C) | human fibrinogen 70% + indocyanine green 0.5% | 113 |
| CONTROL D) | human albumin 25% + indocyanine green 0.5% | 250 |
| 16 | human albumin 12% + sodium hyaluronate 0.5% + indocyanine green 0.5% | 441 |
| 17 | human albumin 25% + dextran 15% + indocyanine green 0.5% | 386 |
| 18 | bovine collagen 13% + sodium hyaluronate 0.3% + indocyanine green 0.5% | 531 |
| 19 | human albumin 8% + sodium hyaluronate 0.7% | 514 |
| 20 | human albumin 25% + collagen (bovine gelatin) 20% | 404 |

As shown in Table 8, compositions of the present invention exhibited a mean tensile strength far exceeding the tensile strength of the protein (human fibrinogen or albumin) alone.

EXAMPLE 21

A composition in accordance with the present invention was tested on three patients in accordance with the following. The patient population comprised end-stage renal disease patients requiring arteriovenus fistula for vascular access for hemodialysis. Consent for experimental treatment was obtained under an approved Institutional Review Board protocol. Using standard techniques the radial artery and a suitable forearm vein were isolated. 6-7 mm anastomoses were created between the artery and vein using a loop of 6 mm Gortex TM graft (standard wall). In one group of patients, this was reinforced with a glue mixture of 25% albumin (New York Blood Center) and a 10 mg/ml solution of Healon TM (Pharmacia) in a 1:2 proportion, with the addition of Fluorescein dye (2 gtts, 5 mg/ml). The glue was sealed to the edge of the anastomosis and suture holes using a KTP laser (532 nm, 1 mm spot size, 500 mW).

The other group of patients received no laser or glue treatment after completion of the sutured anastomosis. After unclamping, any blood leaking from the anastomosis was removed from the field with gauze sponges until bleeding ceased. By subtracting the initial weight of these sponges from the weight after use, the total blood loss from each anastomosis was obtained. The bleeding time was recorded as well and the results are shown in Table 9.

TABLE 9

| Treatment Group | Gortex TM AVF with composition |
|---|---|
| Mean Blood Loss | Mean Bleeding Time |
| 14.7 g | 4 min |
| Control Group | Gortex AVF without composition |
| Mean Blood Loss | Mean Bleeding Time |
| 24.0 g | 4 min |

Overall, the total blood loss was reduced with the composition of the present invention. As expected, the time to form a clot in any unsealed holes remained the same in the treatment and control groups.

We claim:

1. A platelet-free composition for bonding separated tissues together or for coating tissues or prosthetic materials comprising:
   (a) at least one first component in an amount of at least 4.2% by weight based on the total weight of the composition, said first component being selected from the group consisting of naturally occurring peptides, synthetic peptides, and mixtures thereof; and
   (b) at least one second component, which is different than the first component, adapted to support the first component to form a matrix, sol or gel with the first component.

2. The composition of claim 1 wherein the peptides are selected from simple proteins, conjugated proteins, and mixtures thereof.

3. The composition of claim 2, wherein the proteins are selected from the globular proteins, fibrous or structural proteins, and mixtures thereof.

4. The composition of claim 3, wherein the globular proteins are selected from synthetic or naturally occurring or synthetic serum proteins, salts thereof, and mixtures thereof.

5. The composition of claim 4 wherein the serum proteins are selected from albumin, α-globulins, β-globulins, γ-globulins, transthyretin, fibrinogen, and thrombin.

6. The composition of claim 3, wherein the fibrous or structural proteins are selected from synthetic or naturally occurring collagen, elastin, keratin, fibroin, fibrin, fibronectin, salts thereof, and mixtures thereof.

7. The composition of claim 1 wherein the amount of the peptide is in the range of from about 4.2% to 70% by weight.

8. The composition of claim 7 wherein the amount of the peptide is from about 8 to 35% by weight.

9. The composition of claim 1 wherein the second component is selected from naturally occurring or synthetic proteoglycans, glycoproteins, saccharides, polyalcohols, protein gels, gelatins, salts thereof, and mixtures thereof.

10. The composition of claim 9 wherein the proteoglycans are selected from naturally occurring or synthetic non-cellular body matrix materials found in the interstices between cells.

11. The composition of claim 10 wherein said body matrix materials are selected from at least one glycosaminoglycan.

12. The composition of claim 11 wherein the glycosaminoglycans are selected from the group consisting of hyaluronic acid and salts thereof, chondroitin sulfate, dermatan sulfate, keratan sulfate, heparin, and heparan, sulfate.

13. The composition of claim 9 wherein the protein gel is collagen.

14. The composition of claim 9 wherein the saccharides are selected from cellulose compounds, fructose, dextrans, agarose, alginic acid and pectins.

15. The composition of claim 14 wherein the cellulose compounds are selected from methylcellulose, hydroxycellulose, hydroxypropylmethylcellulose, hydroxyethylcellulose and carboxymethylcellulose.

16. The composition of claim 9 wherein the polyalcohol is selected from glycerine, mannitol, sorbitol, polyvinyl alcohol, and polyethylene glycol.

17. The composition of claim 9 wherein the amount of the proteoglycan is in the range of from about 0.1 to 20% by weight.

18. The composition of claim 9 wherein the amount of the glycosaminoglycan is from about 0.1 to 20% by weight.

19. The composition of claim 9 wherein the amount of the saccharide is in the range of from about 0.1 to 70% by weight.

20. The composition of claim 9 wherein the amount of the polyalcohol is in the range of from about 0.1 to 90% by weight.

21. The composition of claim 9 wherein the amount of the protein gel or gelatin is in the range of from about 5 to 80% by weight.

22. The composition of claim 9 wherein the protein gel or gelatin is collagen.

23. The composition of claim 1 wherein component (a) is albumin and component (b) is collagen.

24. The composition of claim 1 wherein component (a) is albumin and component (b) is hyaluronic acid or salt thereof.

25. The composition of claim 1 further comprising at least one additive selected from a viscosity modifier, bonding enhancer, pH modifier, surfactant antioxidant, osmotic agent, and preservative.

26. The composition of claim 25 wherein the amount of additive is no more than about 65% by weight.

27. The composition of claim 1 wherein the composition is adapted to bond separated tissues together and has a viscosity in the range of from about 1,000 to 1,000,000 centipoise.

28. The composition of claim 1 wherein the composition is adapted to coat said tissues of prosthetic materials and has a viscosity in the range of from about 10 to 1,000 centipoise.

29. The composition of claim 1 further comprising at least one naturally occurring or synthetic chromophore.

30. The composition of claim 29 wherein the chromophore is present in sufficient quantity to allow visualization of the composition.

31. The composition of claim 29 wherein the chromophore is selected from indocyanine green, fluorescein, rose bengal, gentian violet, and methylene blue.

32. The composition of claim 29 wherein the chromophore is present in an amount of from 0.01 to 50% by weight.

33. The composition of claim 1 in the form of a aqueous solution.

34. A method of bonding separated tissue together or coating tissue or prosthetic materials comprising, applying an effective amount of the composition of claim 1 to the surface of said tissue or prosthetic material, and allowing said composition to bond or seal to the tissue or prosthetic material.

35. The method of claim 34 further comprising applying an effective amount of energy and/or photons to said composition to enhance bonding, coating, or sealing of said tissue or prosthetic material.

36. The method of claim 35 wherein the energy and/or photons have a wavelength in the electromagnetic spectrum.

37. The method of claim 35 wherein the energy and/or photons are delivered in the form of continuous or discontinuous electrical energy, microwave energy, infrared radiation, monochromatic coherent light, monochromatic non-coherent light and polychromatic light.

38. The method of claim 35 wherein the composition further comprises at least one chromophore.

39. A composition for bonding separated tissue together or for coating tissues or prosthetic materials comprising:
 (a) a first material selected from albumin, fibrinogen, fibrin, fibrinectin, collagen and mixtures thereof in an amount of 8–35% by weight; and
 (b) a second material selected from hyaluronic acid, sodium salts thereof, chondroitin sulfate, hydroxypropylmethylcellulose, hydroxyethylcellulose, carboxymethylcellulose, in an amount of 0.1 to 20% by weight, said composition having a viscosity in the range of from about 1,000 to 200,000 centipoise.

40. The composition of claim 39 further comprising a chromophore selected from indocyanine green, fluorescein, methylene blue, and rose bengal, in an amount of from 0.01 to 10% by weight.

41. A method of producing a composition for bonding separated tissues together or for coating tissues or prosthetic materials which comprises:
 (a) at least one first component in an amount of at least 4.2% by weight selected from naturally occurring or synthetic peptides, and mixtures thereof; and
 (b) at least one second component, which is different than the first component, adapted to support the first component to form a matrix, sol or gel with the first component; said method comprising:
  (1) combining the first and second components;
  (2) agitating the product obtained from step (1) to form a mixture;
  (3) placing the product step (2) into a vessel adapted to store or deliver the composition.

42. A composition for bonding separated tissues together or for coating tissues or prosthetic materials comprising:
 (a) at least one first component in an amount of at least 4.2% by weight based on the total weight of the composition, said first component being selected from the group consisting of naturally occurring peptides, synthetic peptides and mixture thereof; and (b) at least one second component selected from the group consisting of naturally occurring or synthetic proteoglycans, saccharides, polyalcohols and mixtures thereof.

* * * * *